United States Patent
Kohno et al.

(10) Patent No.: US 10,422,798 B2
(45) Date of Patent: Sep. 24, 2019

(54) IMMUNOCHROMATOGRAPHIC TEST STRIP FOR DETECTING OBJECT IN RED BLOOD CELL-CONTAINING SAMPLE AND IMMUNOCHROMATOGRAPHY USING THE TEST STRIP

(71) Applicant: SEKISUI MEDICAL CO., LTD., Tokyo (JP)

(72) Inventors: Keigo Kohno, Tokyo (JP); Mayumi Yoshida, Tokyo (JP); Mitsuaki Yamamoto, Tokyo (JP); Shinya Yokokawa, Tokyo (JP); Marie Asami, Tokyo (JP)

(73) Assignee: SEKISUI MEDICAL CO., LTD., Tokyo (JP)

( * ) Notice: Subject to any disclaimer, the term of this patent is extended or adjusted under 35 U.S.C. 154(b) by 202 days.

(21) Appl. No.: 15/536,621

(22) PCT Filed: Dec. 16, 2014

(86) PCT No.: PCT/JP2014/083236
§ 371 (c)(1),
(2) Date: Aug. 16, 2017

(87) PCT Pub. No.: WO2016/098177
PCT Pub. Date: Jun. 23, 2016

(65) Prior Publication Data
US 2017/0370926 A1    Dec. 28, 2017

(51) Int. Cl.
*G01N 33/543* (2006.01)
*G01N 33/558* (2006.01)

(52) U.S. Cl.
CPC ..... *G01N 33/54393* (2013.01); *G01N 33/543* (2013.01); *G01N 33/54386* (2013.01); *G01N 33/558* (2013.01)

(58) Field of Classification Search
None
See application file for complete search history.

(56) References Cited

U.S. PATENT DOCUMENTS 5,262,067 A    11/1993  Wilk et al.
2001/0006823 A1  7/2001  Yoshimura et al.
(Continued)

FOREIGN PATENT DOCUMENTS

EP    0392377 A2    10/1990
EP    0392377 A3    10/1990
(Continued)

OTHER PUBLICATIONS

Machine Translation of JP-2013-252483-A, published Dec. 19, 2013 (English language version only provided).
(Continued)

*Primary Examiner* — Erik B Crawford
(74) *Attorney, Agent, or Firm* — Birch, Stewart, Kolasch & Birch, LLP

(57) ABSTRACT

A problem of the present invention is to provide an immunochromatographic test strip avoiding agglutination of colloidal gold while red blood cells in whole blood are agglutinated and then separated and removed in the case of using polybrene as a hemagglutinating agent and the colloidal gold conjugates as a detection reagent, and to provide immunochromatography using the test strip. To solve the problem, the present inventors reviewed the composition of the existing reagent itself from a completely different viewpoint rather than the selection of type or amount of polyanions, and as a result of extensive study on each element, the inventors surprisingly found that agglutination of colloidal gold may be suppressed by using a particular additive without neutralization by polyanions.

5 Claims, 15 Drawing Sheets

(56) References Cited

U.S. PATENT DOCUMENTS

| | | |
|---|---|---|
| 2004/0161857 A1 | 8/2004 | Yugawa et al. |
| 2009/0209661 A1 | 8/2009 | Somerville Roberts et al. |
| 2011/0117636 A1 | 5/2011 | Bae et al. |
| 2013/0011932 A1* | 1/2013 | Itoh .................. G01N 33/54393 436/501 |
| 2015/0086974 A1 | 3/2015 | Yoshida et al. |

FOREIGN PATENT DOCUMENTS

| | | |
|---|---|---|
| EP | 0457183 A1 | 11/1991 |
| EP | 0392377 B1 | 2/1995 |
| EP | 0457183 B1 | 8/1995 |
| EP | 2 317 319 A1 | 5/2011 |
| EP | 2 523 001 A1 | 11/2012 |
| JP | 3-205563 A | 9/1991 |
| JP | 5-99918 A | 4/1993 |
| JP | 2002-509254 A | 3/2002 |
| JP | 2011-511876 A | 4/2011 |
| JP | 2013-252483 A | 12/2013 |
| WO | WO 03/085402 A1 | 10/2003 |
| WO | WO 2013/147307 A1 | 10/2013 |

OTHER PUBLICATIONS

Office Action dated Oct. 31, 2018, in Chinese Patent Application No. 201480084630.X, with English translation.
Extended European Search Report dated Aug. 16, 2018, in European Patent Application No. 14908387.5.
English translation of International Preliminary Report on Patentability and Written Opinion dated Jun. 29, 2017, in PCT International Application No. PCT/JP2014/083236.

* cited by examiner

[FIG. 1-1]
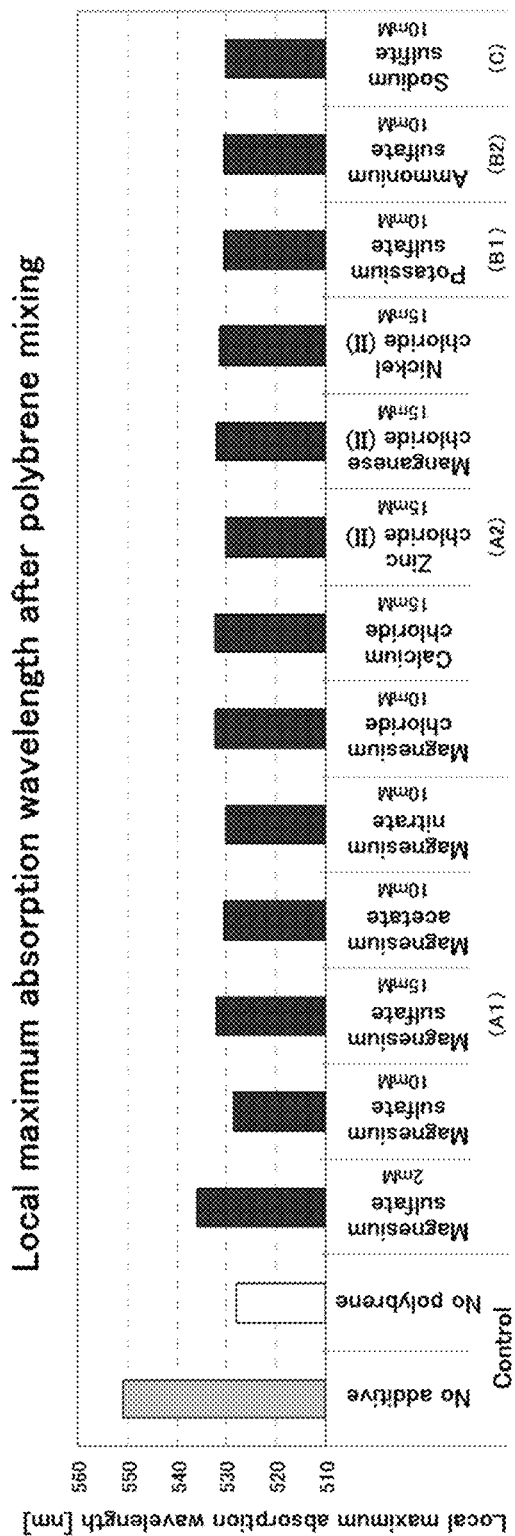

[FIG. 1-2]
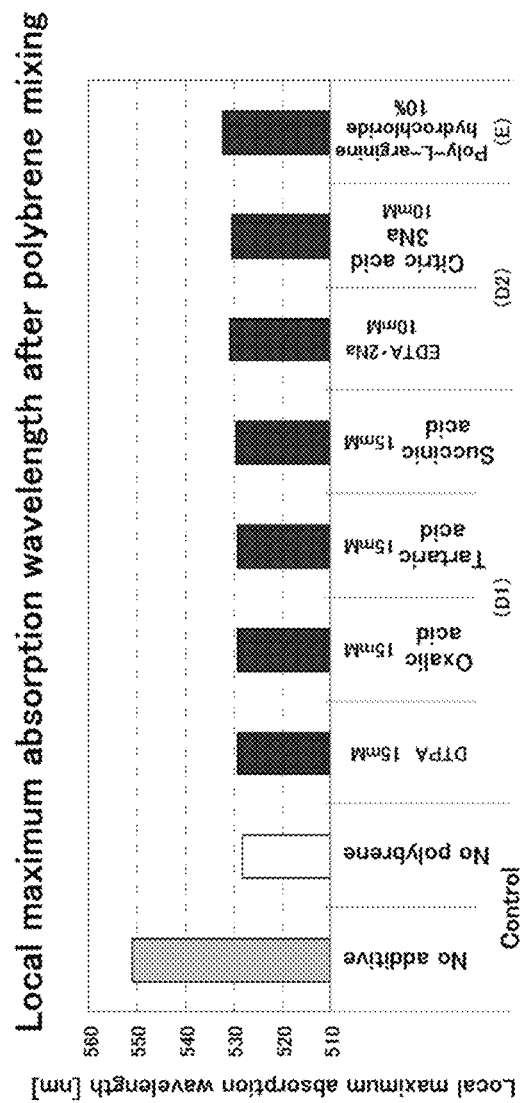

[FIG. 1-3]
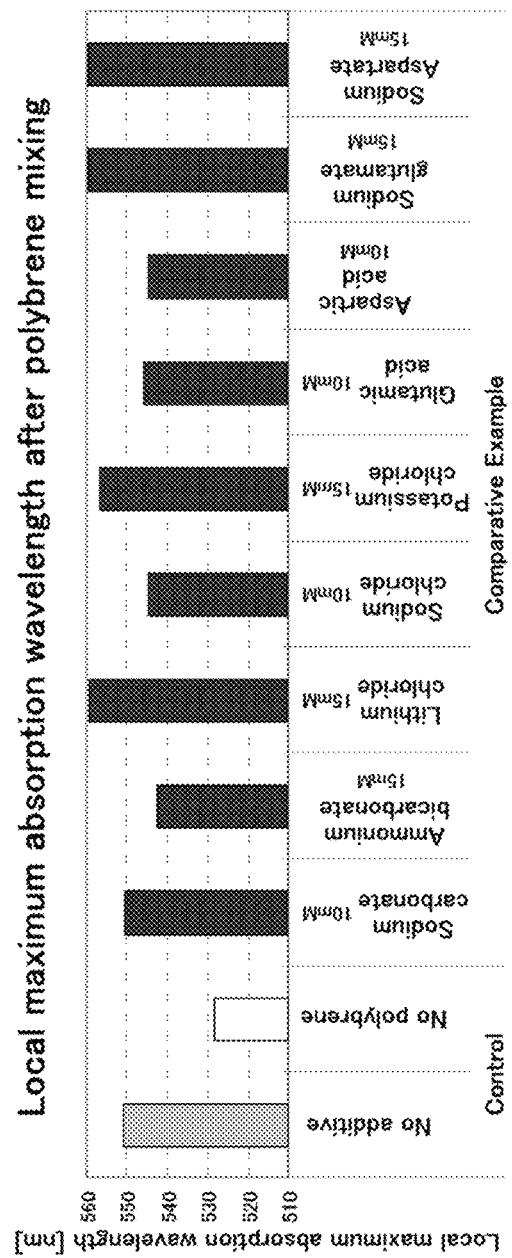

[FIG. 2]
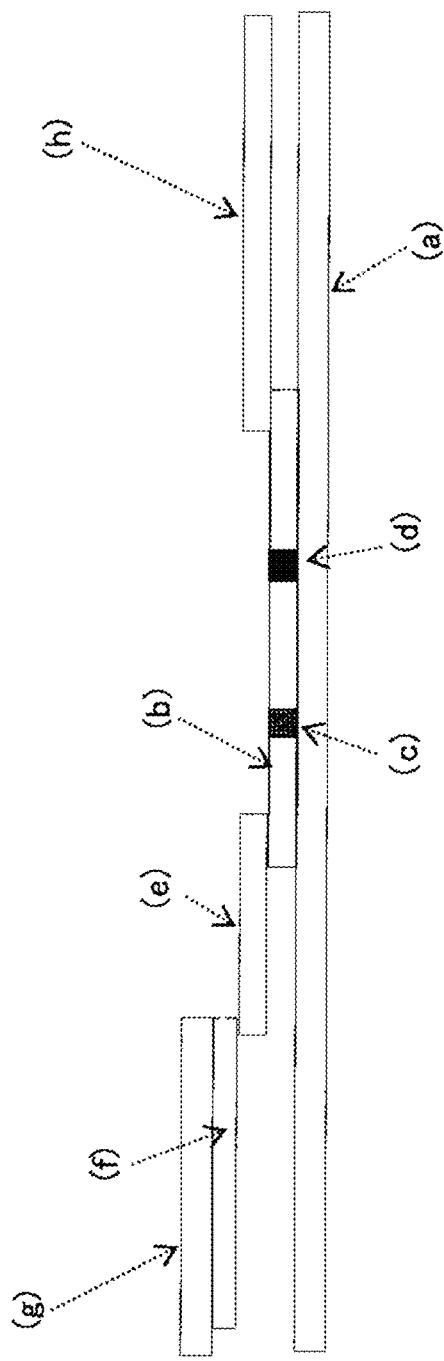

[FIG. 3A-1]
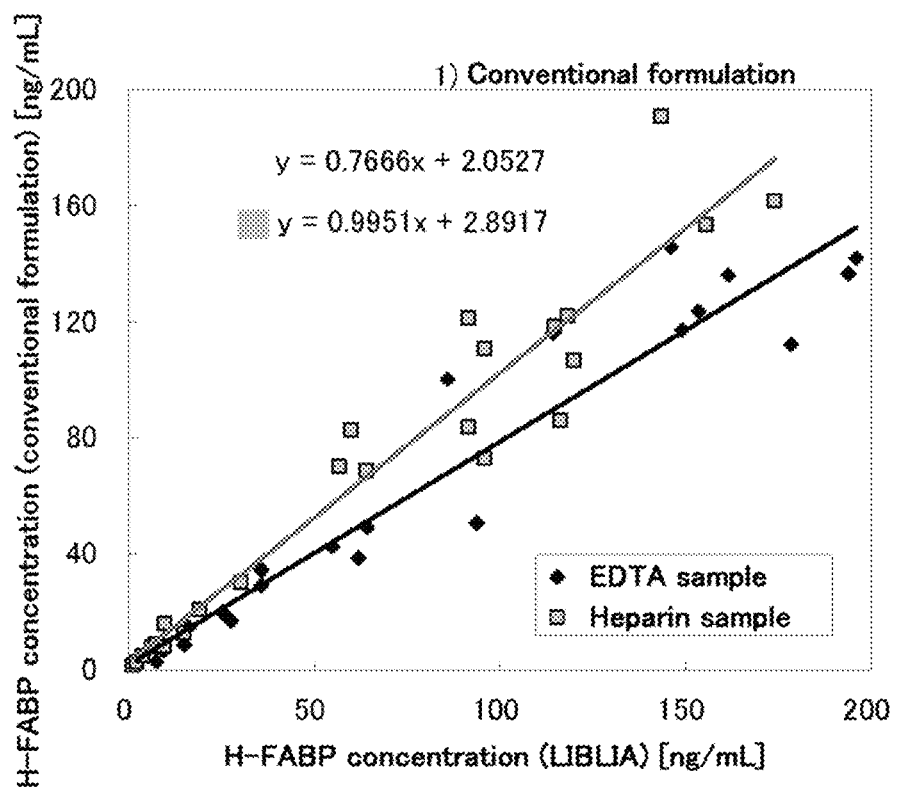

[FIG. 3A-2]
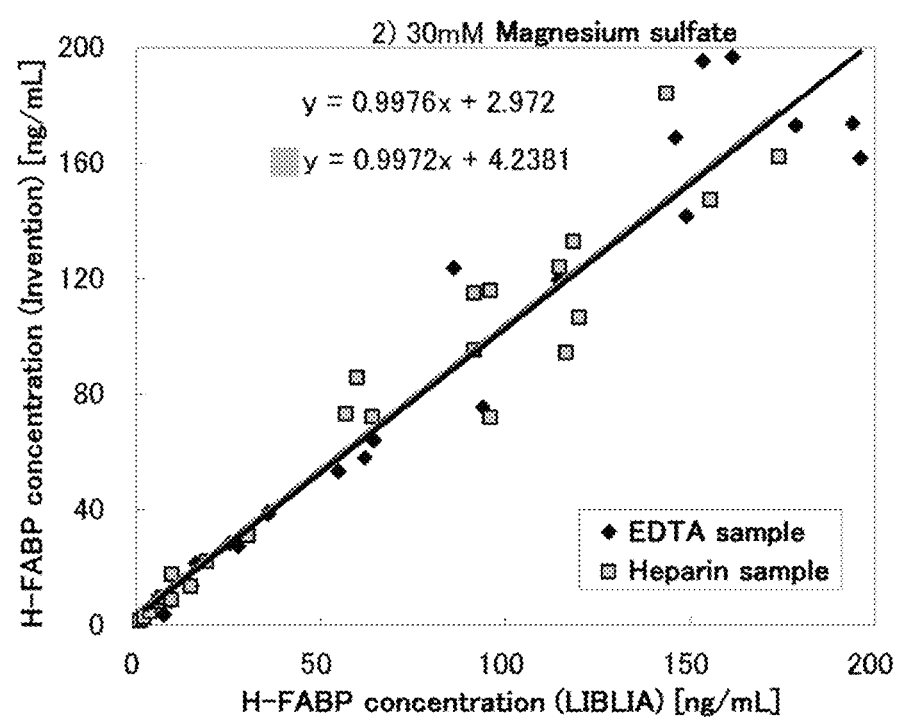

[FIG. 3A-3]
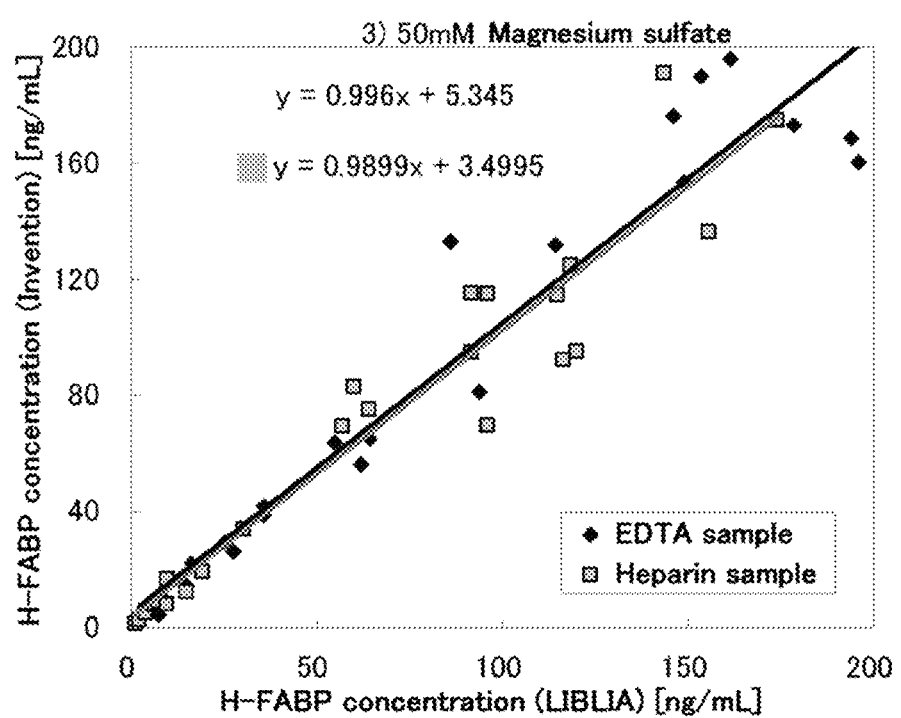

[FIG. 3A-4]
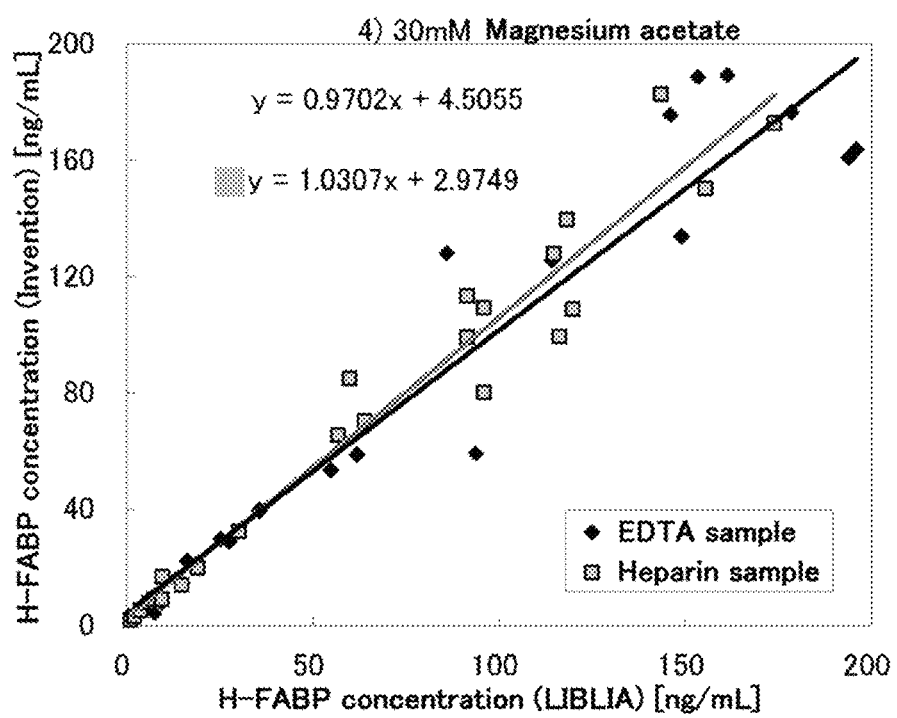

[FIG. 3A-5]
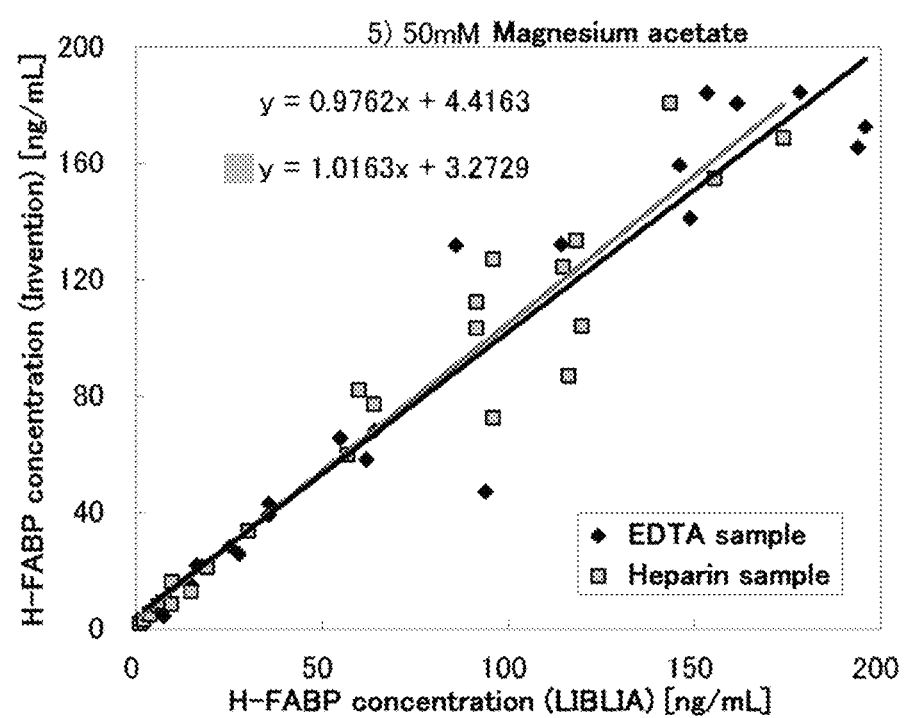

[FIG. 3A-6]
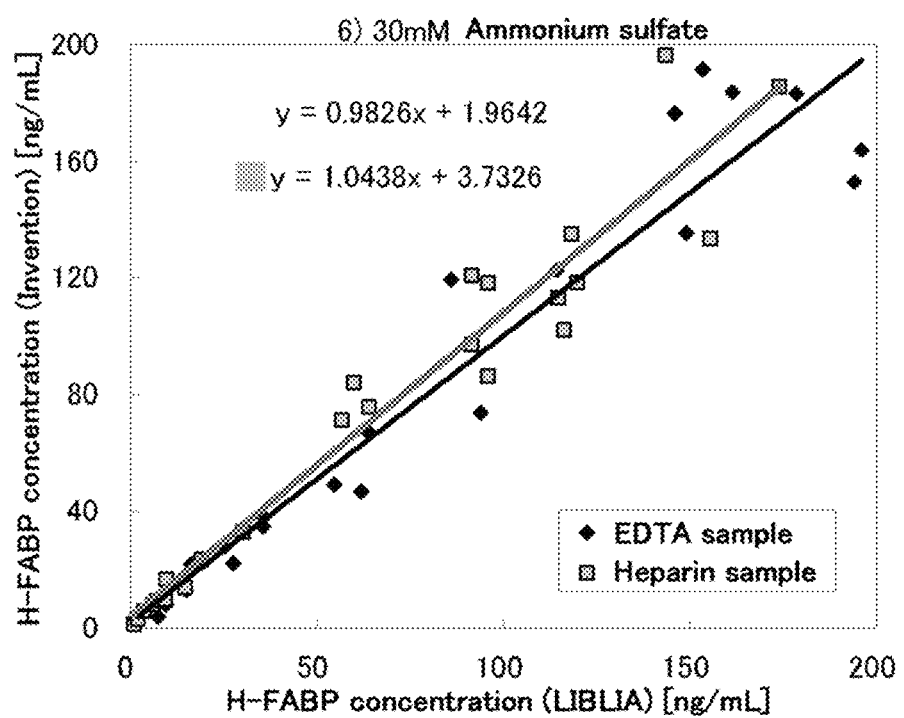

[FIG. 3B-1]
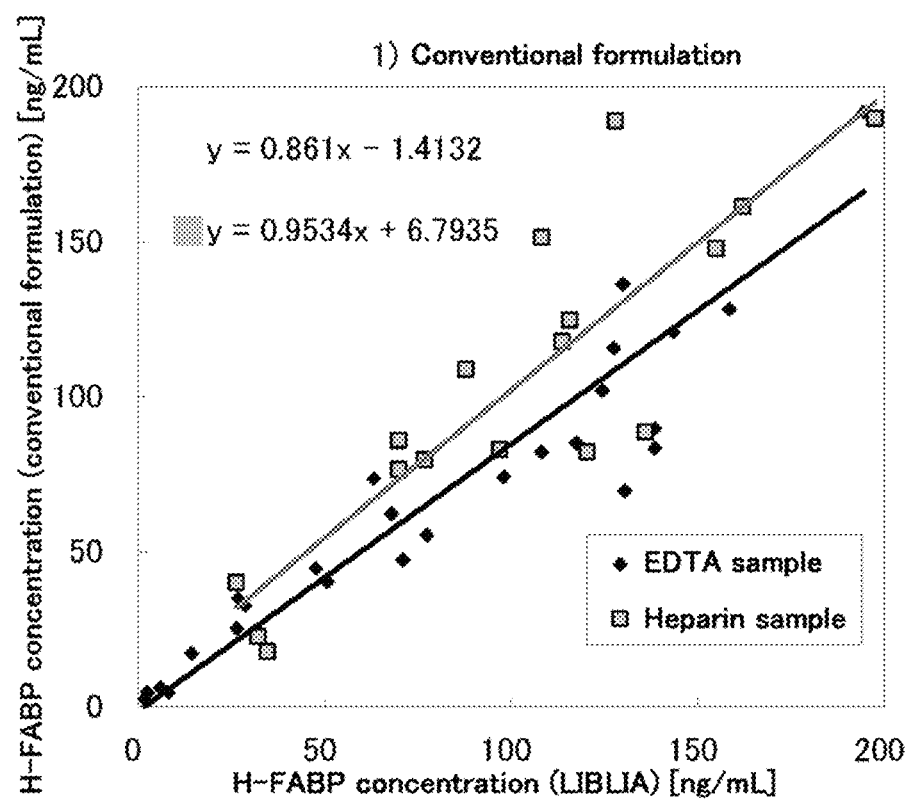

[FIG. 3B-2]
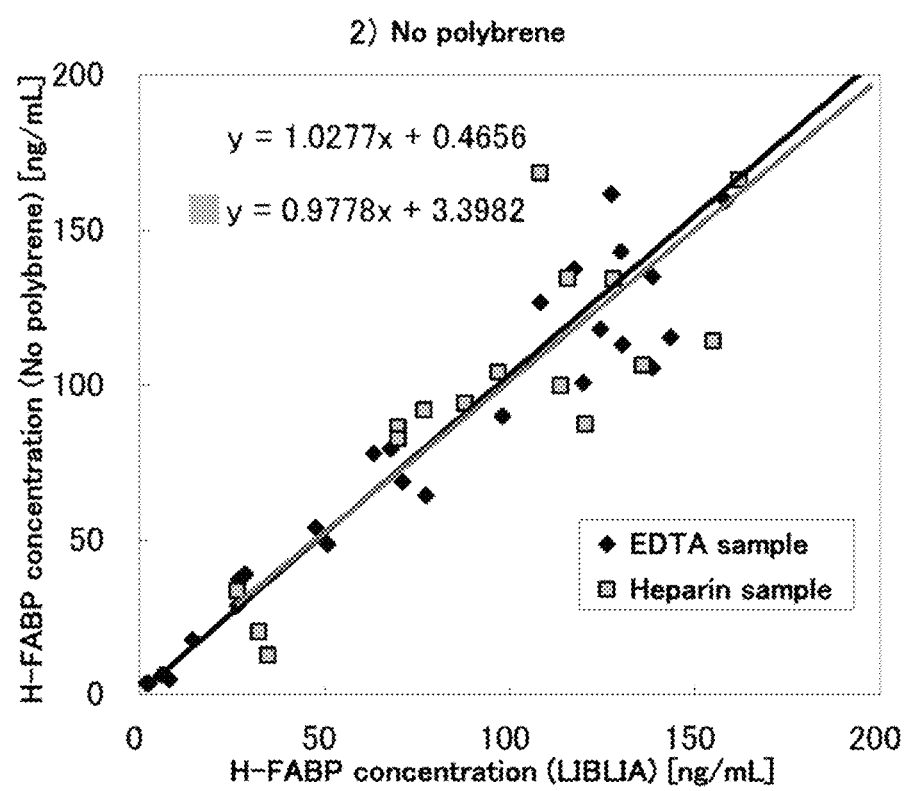

[FIG. 3B-3]
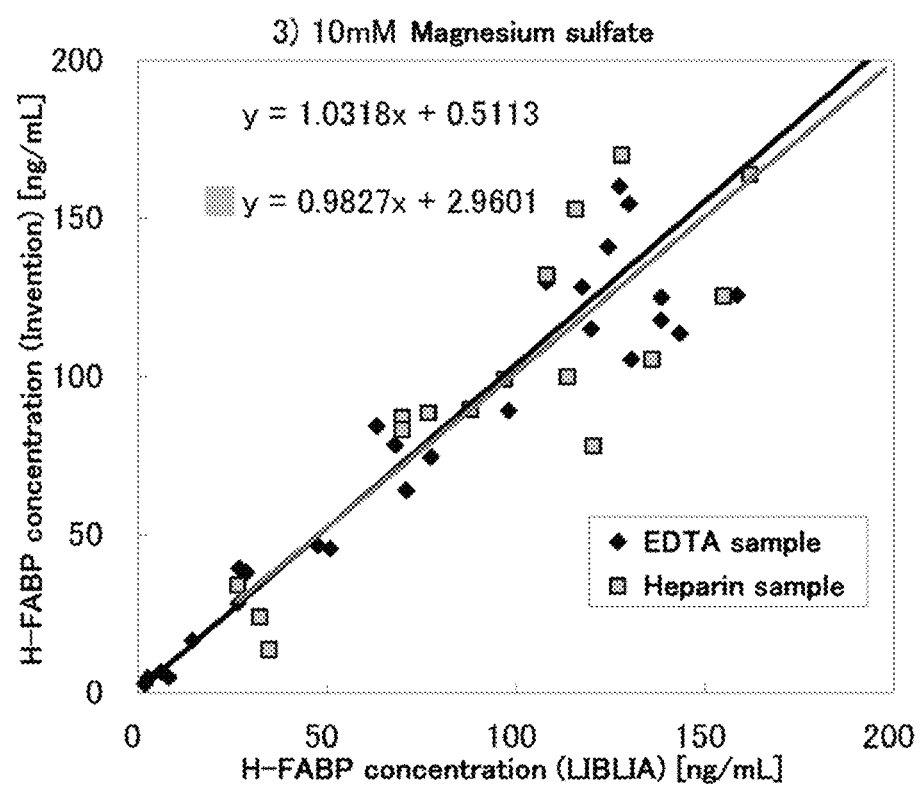

[FIG. 4A]
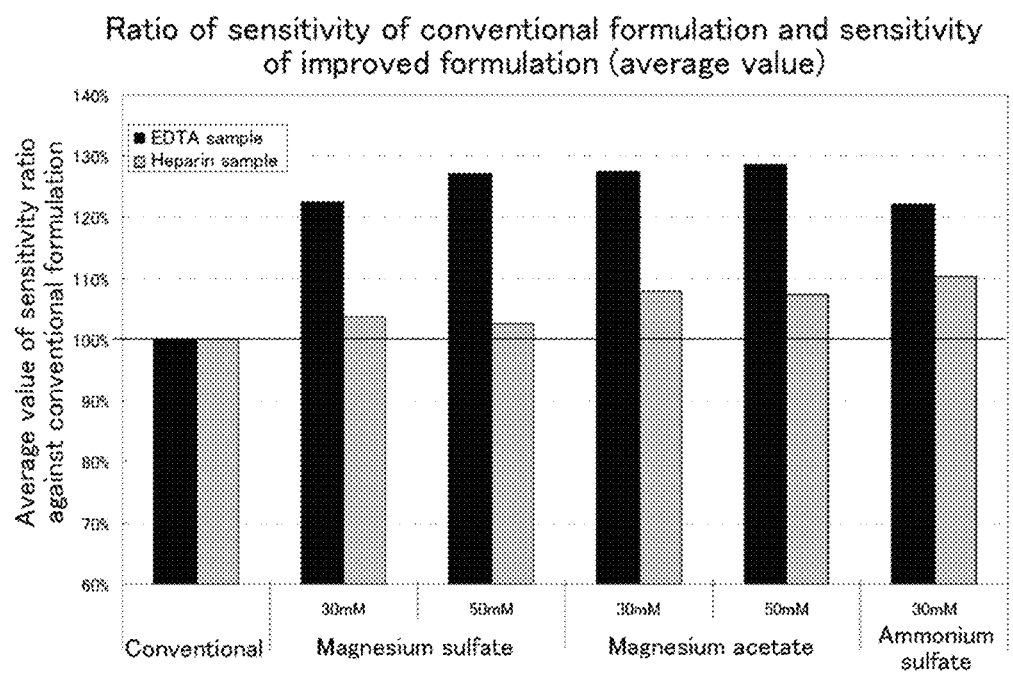

[FIG. 4B]
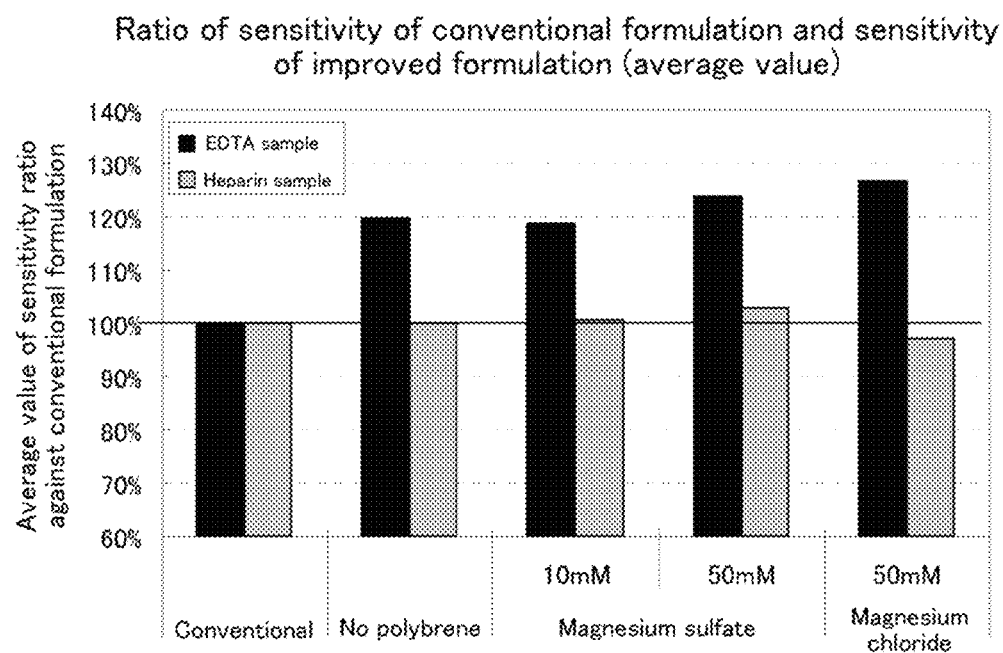

IMMUNOCHROMATOGRAPHIC TEST STRIP FOR DETECTING OBJECT IN RED BLOOD CELL-CONTAINING SAMPLE AND IMMUNOCHROMATOGRAPHY USING THE TEST STRIP

TECHNICAL FIELD

The present invention relates to an immunochromatographic test strip for detecting an object in a red blood cell-containing sample, and immunochromatography using the test strip. More particularly, the present invention relates to a test strip which is treated with a particular additive to avoid nonspecific agglutination of colloidal gold conjugates acting as a detection reagent due to the presence of a hemagglutinating agent even when the hemagglutinating agent containing a polycation as an active ingredient coexists in a measurement system, and immunochromatography using the test strip.

BACKGROUND ART

In recent years, the need to "know examination results while examining a patient" has increased in clinics and small-scale hospitals, and thus switching from conventional outsourced examination done outside hospitals to Point of Care Testing (POCT) occurs. With the spread of POCT, a device installing an immunochromatographic lateral flow test strip is being used as an in vitro diagnostic product. An immunochromatographic test strip enables detection of an object in a sample, without the need of reagent preparation at the time of testing, through only a simple manipulation such as direct dropping of a test sample (hereinafter, referred to as "sample") such as blood, urine, etc. onto the test strip, and is very useful for simple and rapid analysis of an analyte.

The immunochromatographic test strip (hereinafter, referred to as "test strip") is generally a porous membrane including a sample supply portion, a spreading portion, and a detecting portion, and has a structure in which a detection reagent (hereinafter, referred to as "conjugate") such as a labeled antibody against an analyte, etc. is retained at a spreading start part of the spreading portion in a dissolvable and spreadable manner such that the labeled antibody can pass through the spreading portion and reach the detecting portion after contact with a sample while an immobilized antibody is immobilized at a part of the spreading portion to constitute the detecting portion. When the sample is dropped onto the sample supply portion, the analyte in the sample specifically binds to the labeled antibody to form a complex, and the complex spreads through the spreading portion in the downstream direction and further binds to the immobilized antibody. Thus, by detecting a sandwich-type complex of the labeled antibody, the analyte, and the immobilized antibody in an antibody-immobilization part, the analyte may be qualitatively or quantitatively analyzed. An example of a label constituting a conjugate is colloidal gold particles and a color reaction of the colloidal gold particles enables qualitative detection. The analyte in the sample may also quantitatively be detected, based on a degree of coloring.

However, if the sample is whole blood, red blood cells in the whole blood cannot move in a porous membrane, and will problematically clog pores of the membrane and obstruct spreading of the sample. Therefore, if whole blood is used as a sample, red blood cells must preliminarily be separated and removed from the whole blood, and known methods include a method of removing red blood cells after precipitation through centrifugation before measurement, and a method of filtrating and removing red blood cells agglutinated by a red blood cell-separating agent before measurement or at the start of measurement.

As the red blood cell-separating agent, for example, hexadimethrine bromide (distributed under the trade name of polybrene, hereinafter, simply referred to as polybrene) is known (Patent Documents 1, 2, and 3).

In Patent Document 1, polybrene is described as an example of a hemagglutinating agent made of a synthetic water-soluble polymer.

In Patent Document 2, a glass-fiber blood cell-separating membrane for chromatography containing polybrene as a hemagglutinating substance is described. Since passage of blood through the blood cell-separating membrane is associated with hemolysis when polybrene is solely used, a technique is disclosed for coating the blood cell-separating membrane with PVA for avoiding the hemolysis.

Although polybrene is generally known as a hemagglutinating agent, if polybrene is used for immunochromatography employing a metal conjugate as a detection reagent, polybrene problematically causes not only agglutination of red blood cells in whole blood but also agglutination of the metal conjugate (Patent Document 3).

Patent Document 3 discloses a technique for preventing such agglutination of metal conjugates. That is, disclosed in Patent Document 3 is an immunochromatographic assay device that has a polycation, such as polybrene, etc., as a red blood cell-separating agent bound in the upstream of chromatography supports (carriers) and a polyanion for neutralizing the polycation bound in the downstream thereof. According to this technique, agglutination of metal conjugates made of selenium may be prevented, because the positive charge of the polycation is neutralized by the negative charge of the polyanion.

CITATION LIST

Patent Literature

Patent Document 1: Japanese Patent Application Laid-Open No. 3-205563
Patent Document 2: Japanese Patent Application Laid-Open No. 5-099918
Patent Document 3: Japanese Patent Application No. 2002-509254

SUMMARY OF INVENTION

Technical Problem

When immunochromatography was practiced using whole blood as a sample and employing polybrene as a hemagglutinating agent and a colloidal gold conjugate as a detection reagent, the present inventors attempted to neutralize positive charge of polybrene by adding polyanions so as to prevent agglutination of the colloidal gold conjugate in accordance with the disclosure of Patent Document 3. However, although the red blood cells in the whole blood could be agglutinated and then separated and removed, the agglutination of colloidal gold conjugates could not be prevented. Although the reason is uncertain, this may be attributable to the difference between selenium conjugates of Patent Document 3 and colloidal gold conjugates, and the difference in the type of polyanions, etc.

A problem of the present invention is to provide an immunochromatographic test strip avoiding agglutination of colloidal gold conjugates while red blood cells in blood are agglutinated and then separated and removed in the case of using polybrene as a hemagglutinating agent containing polycation as an active ingredient and the colloidal gold conjugates as a detection reagent, and to provide immunochromatography using the test strip.

Solution to Problem

In order to study the method of solving the problem, the present inventors have reviewed the composition of the existing reagent itself from a completely different viewpoint rather than the selection of type or amount of polycations that are materials causing the problem, and as a result of extensive study on each constituent element, the present inventors surprisingly found that there exists an additive having an ability to suppress agglutination of colloidal gold conjugates by polybrene, and the additive may be used to suppress the agglutination of colloidal gold conjugates without relying on the neutralization of polycations by polyanions, thereby completed the present invention. That is, the present invention has the following configuration:

[1] An immunochromatographic test strip comprising the following configuration:

(1) a membrane consisting of a porous body equipped with at least a sample supply portion, a spreading portion, and a detecting portion, wherein a part of the spreading portion comprises a conjugate-retaining part where a conjugate of an anti-analyte antibody labeled with colloidal gold is retained in a dissoluble manner, and an immobilized antibody is immobilized in the detecting portion which is a part of the spreading portion on the downstream side relative to the conjugate-retaining part, and (2) an additive for suppressing agglutination of the conjugate due to polybrene acting as a hemagglutinating agent, wherein the additive is contained at least in a part of from the sample supply portion to an upstream side of the conjugate-retaining part of the spreading portion so as to be capable of contacting with polybrene that is provided through the sample supply portion,

[2] The test strip of item [1] above, wherein polybrene is contained in the sample supply portion.

[3] The test strip of item [1] or [2] above, wherein the additive is contained in the conjugate-retaining part.

[4] The test strip of any one of items [1] to [3] above, wherein a polyanion as a neutralizer for neutralizing a cation of polybrene acting as a hemagglutinating agent is not included.

[5] The test strip of any one of items [1] to [4] above, wherein the additive is one or two or more compounds selected from the group consisting of (A) a salt of a divalent metal, (B) a salt of sulfuric acid with a metal or onium, (C) a salt of sulfurous acid with a metal, (D) a carboxylic acid chelator, and (E) a polybasic amino acid.

[6] A detection method of using immunochromatography, comprising the steps of:

(A) supplying a sample to a sample supply portion of a test strip comprising a membrane consisting of a porous body equipped with at least a sample supply portion, a spreading portion, and a detecting portion, wherein a part of the spreading portion comprises a conjugate-retaining part where a conjugate of an anti-analyte antibody immobilized on colloidal gold is retained in a dissoluble manner, and an immobilized antibody is immobilized in the detecting portion which is a part of the spreading portion on the downstream side relative to the conjugate-retaining part;

(B) agglutinating a blood-derived component in the sample through contact between polybrene and the sample in the sample supply portion or in the upstream of the sample supply portion;

(C) separating and removing aggregates obtained in step (B) from the sample;

(D) bringing a sample component obtained in step (C), from which the aggregates are separated and removed, into contact with the colloidal gold-containing conjugate, this step being performed in the presence of an additive having an ability to suppress agglutination of the conjugate due to polybrene; and (E) detecting a complex of the object in the sample component and the conjugate obtained in step (D) in the detecting portion.

[7] The detection method of item [6] above, wherein polybrene is contained in the sample supply portion.

[8] The detection method of item [6] or [7] above, wherein the additive is contained in the conjugate-retaining part.

[9] The detection method of any one of items [6] to [8] above, wherein a polyanion as a neutralizer for neutralizing the cation of polybrene acting as a hemagglutinating agent is not included.

[10] The detection method of any one of items [6] to [9] above, wherein the sample is a heparinized-blood sample or an EDTA blood sample.

[11] The detection method of any one of items [6] to [10] above, wherein the additive is one or two or more compounds selected from the group consisting of (A) a salt of a divalent metal, (B) a salt of sulfuric acid with a metal or onium, (C) a salt of sulfurous acid with a metal, (D) a carboxylic acid chelator, and (E) a polybasic amino acid.

Advantageous Effects of Invention

According to the present invention, in immunochromatography using polybrene as a hemagglutinating agent and a colloidal gold conjugate as a detection reagent, only red blood cells may be agglutinated and then separated and removed from the sample without agglutination of the colloidal gold conjugate by using an additive having an ability to suppress agglutination of the colloidal gold conjugate due to polybrene, whereby the colloidal gold conjugate may play the original role of the detection reagent, and therefore, an analyte in the sample may accurately be detected and measured. Since addition of a polyanion as a polycation-neutralizer is not an essential condition, a reagent composition may be made extremely simple, and the present invention advantageously leads to reduction of factors which may cause unpredictable effects on the immunoreaction and the spread of the analyte on the strip.

BRIEF DESCRIPTION OF DRAWINGS

FIG. 1 is a diagram showing results of measuring a local maximum absorption wavelength of a mixed solution of a polybrene solution and a conjugate solution to which additive candidates of the present invention were added (Example 1);

FIG. 2 shows a schematic structure of an immunochromatographic test strip of the present invention;

FIG. 3 is a diagram showing a comparison between an immunochromatographic method using the additives of the present invention and an LTIA method (Example 2); and FIG. 4 is a diagram showing a comparison of the detection sensitivity between an additive formulation of the present invention and a conventional formulation (Example 3).

DESCRIPTION OF EMBODIMENTS (Immunochromatographic Test Strip)

An immunochromatographic test strip of the present invention is a porous membrane equipped with at least a "sample supply portion", a "spreading portion", and a "detecting portion", and has a structure in which a labeled antibody against an analyte is retained at a spreading start part of the spreading portion in a dissoluble manner such that the labeled antibody passes through the spreading portion and reaches the detecting portion after contact with a sample while an immobilized antibody is immobilized at a part of the spreading portion to constitute the detecting portion. An example of embodying these elements may be a test strip including a sample pad that serves as the sample supply portion, a conjugate pad that has a labeled antibody against an analyte retained in a dissoluble manner and plays a part of the spreading portion, and a porous membrane that has an immobilized antibody immobilized at a part thereof and serves as the spreading portion and the detecting portion. That is, a typical immunochromatographic test strip of the present invention has the following configuration:

(1) a sample pad to which a sample is supplied;
(2) a conjugate pad which is disposed in the downstream of the sample pad and retains a conjugate in a dissoluble manner, the conjugate having a first antibody sensitized on a colloidal gold surface; and
(3) a porous membrane which is disposed in the downstream of the conjugate pad and immobilizes a second antibody binding to a complex of the conjugate and an analyte, wherein the sample pad, the conjugate pad, and the porous membrane may constitute respective different supports, or two of the elements may constitute one support, and may take any form as long as the sample pad, the conjugate pad, and the porous membrane are arranged in this order from the upstream toward the downstream.

The immunochromatographic test strip may be a strip further having any one or more of an absorption pad and a 3rd pad disposed and mounted along with the above constituents. The test strip is usually disposed on a solid phase support such as a plastic adhesive sheet. It is obvious that the solid phase support is made of a material not hindering the capillary flow of the sample and an adhesive component is made of a material not hindering the capillary flow of the sample. Further, the test strip may be laminated with a polyester film, etc., for the purpose of increasing the mechanical strength of the antibody-immobilized porous membrane and preventing evaporation (drying) of water during an assay.

(Hemagglutinating Agent)

As a hemagglutinating agent used in the present invention, a known polycationic hemagglutinating agent may be used. In particular, polybrene is preferred. Polybrene has a chemical name of hexadimethrine bromide and is one of cationic polymers, having CAS No. 28728-55-4.

In the present invention, polybrene is used for agglutinating red blood cells in whole blood used as a sample. With regard to the manner of using polybrene, polybrene may be added to a diluent which dilutes the sample or may directly be added to the sample, and in other cases, polybrene may be contained in the sample supply portion (sample pad) of the immunochromatographic strip. In such usage forms, polybrene comes into contact with whole blood and the red blood cells in the whole blood are agglutinated. The aggregates of red blood cells are removed through some kind of filtration, and are removed in the immunochromatographic strip by the sample supply portion on which a large portion of the red blood cell aggregates remains when the sample passes through a filter constituting the sample supply portion. In the present invention, a 3rd pad (blood cell-separating membrane) described below is desirably used together to remove the red blood cell aggregates in the sample supply portion and to more certainly reduce the red blood cell aggregates supplied to the spreading portion.

The addition amount of polybrene may be any amount capable of agglutinating, separating, and removing red blood cells of whole blood so that an analyte in a whole blood sample can spread in a desirable manner, and for example, if polybrene is contained in the sample pad, the concentration is preferably 0.25% or more, and more preferably 0.25% to 2% relative to the fluid volume of the sample to be dropped. In terms of manufacturing of the sample pad, the concentration of polybrene in the solution impregnated into the pad is preferably 0.5% or more, and more preferably 0.5% to 4%.

In addition, although polyanions are not included in the present invention, unlike Patent Document 3, as a neutralizer for neutralizing cations of polybrene acting as a hemagglutinating agent, the presence of polyanions is not excluded as long as the polyanions are normally used as needed within a range not affecting the reaction system without departing from the object of the present invention.

(Additive)

Although a hemagglutinating agent (polybrene) is used for the purpose of agglutinating red blood cells in a whole blood sample in the present invention, polybrene has a problem of causing agglutination of not only the red blood cells but also colloidal gold conjugates. In the present invention, an additive must be used so as to avoid such agglutination of the colloidal gold conjugates.

The additive used in the present invention may be any additive as long as it has an ability to suppress agglutination of colloidal gold conjugates due to polybrene.

Additives having such ability are, for example, added to a solution containing the colloidal gold conjugates and polybrene, and whether or not the additives exhibit the effect of suppressing agglutination of the conjugates is examined, whereby the additive of the present invention may be selected. More specifically, this selection method is a method of adding an additive solution to be selected to the colloidal gold conjugates, adding the polybrene solution thereto, measuring a local maximum absorption wavelength, and selecting an additive which has a local maximum absorption wavelength smaller than that in the case of no additive.

Particularly, it is surprising that the additive may selectively agglutinate only one of the two kinds of polyanions, i.e., the colloidal gold conjugates and the red blood cells, and may suppress the agglutination of the other in the coexistence state.

The additive selected by the above selection method may be one or two or more compounds selected from the group consisting of (A) a salt of a divalent metal, (B) a salt of sulfuric acid with a metal or onium, (C) a salt of sulfurous acid with a metal, (D) a carboxylic acid chelator, and (E) a polybasic amino acid.

(A) Salt of Divalent Metal

The salt of divalent metal may be further classified into (A1) a salt of a divalent metal with an acid, and (A2) a salt of a divalent metal with a halogen element. Here, the divalent metal may be exemplified by magnesium, calcium, nickel, zinc, etc. The acid may be exemplified by inorganic acids such as sulfuric acid, nitric acid, etc., and organic acids such as acetic acid, etc. The halogen element may be exemplified by chlorine, bromine, etc. Among them, magnesium sulfate, magnesium nitrate, and magnesium acetate are preferred as specific compounds of (A1), and magnesium chloride, calcium chloride, zinc chloride, manganese chloride, and nickel chloride are preferred as specific compounds of (A2).

(B) Salt of Sulfuric Acid With Metal or Onium

The (B1) salt of sulfuric acid with a metal may include a salt of sulfuric acid with a monovalent metal or a salt of sulfuric acid with a divalent metal, and in particular, potassium sulfate and magnesium sulfate (overlapped with A1) are preferred. The (B2) salt of sulfuric acid with an onium is preferably ammonium sulfate.

(C) Salt of Sulfurous Acid With Metal

The salt of sulfurous acid with a metal is preferably sodium sulfite.

(D) Carboxylic Acid Chelator and Salt Thereof

The carboxylic acid chelator may be further classified into (D1) dicarboxylic acid chelators, (D2) tricarboxylic acid chelators, (D3) tetracarboxylic acid chelators, and (D4) pentacarboxylic acid chelators. The (D1) dicarboxylic acid chelator is preferably oxalic acid, succinic acid, and tartaric acid, the (D2) tricarboxylic acid chelator is preferably citric acid, the (D3) tetracarboxylic acid chelator is preferably ethylenediaminetetraacetic acid (EDTA), and the (D4) pentacarboxylic acid chelator is preferably diethyltriamine pentaacetic acid (DTPA). These chelators may be used as free acids or metal salts. In the case of being used as metal salts, specific example thereof may include trisodium citrate, disodium EDTA, etc. In addition to the above compounds, it is also possible to modify or alter a part of a structure of the above compound, such as glycol ether diamine tetraacetic acid (EGTA), etc.

(E) Polybasic Amino Acid

The polybasic amino acid may be exemplified by poly-L-arginine, and poly-L-arginine hydrochloride is preferably used. Poly-L-arginine hydrochloride is a compound that is classified as a red blood cell-separating agent having a positive charge, like polybrene in Patent Document 3, and it is surprising that when poly-L-arginine hydrochloride is used together with polybrene, the aggregating effect of colloidal gold conjugates due to polybrene is not enhanced but reduced.

The addition amount of the additive may be any amount capable of suppressing agglutination of the colloidal gold conjugates due to polybrene, and for example, the concentration of the solution impregnated into a sample pad and/or a conjugate pad may be 1 mmol/L to 100 mmol/L, and preferably 2 mmol/L to 50 mmol/L, 10 mmol/L to 50 mmol/L. The kind, addition amount, and concentration of the additive may be appropriately determined depending on the analyte of interest, necessary sensitivity, etc.

The usage form of the particular additive of the present invention may be any form as long as it is able to suppress agglutination of colloidal gold conjugates due to polybrene as a hemagglutinating agent, and the additive may be impregnated into at least a portion of the immunochromatographic test strip from the sample supply portion to the conjugate immobilization part of the spreading portion so as to be capable of contacting with the polybrene component. Therefore, the additive may be impregnated into only the sample supply portion or into the entire part of from the sample supply portion to the spreading portion.

The form of the sample-supplying and/or conjugate pad(s) containing the additive includes a form in which a liquid additive is contained in the pad(s) as well as a form in which the pad(s) is/are dried after the additive is impregnated into the pad(s) such that the additive is attached to the pad(s) in a dry state.

The particular additive of the present invention may be also used by adding the additive to a sample-diluting solution.

Although a particular additive must be used in a particular usage form in the present invention as described above, this does not prevent use of other additive than those described above for another purpose, or use of an additive in another usage form other than those described above. For example, a form, in which a particular additive of the present invention is impregnated into from the sample supply portion to the conjugate immobilization part of the spreading portion while an antibody-immobilization part of the spreading portion is impregnated with other additive than those described above, is obviously included within the scope of the present invention.

(Colloidal Gold)

Colloidal gold used as a label in the present invention may be any colloidal gold as long as it is able to form a conjugate through sensitization with (immobilization of) an antibody and to serve as a label in a method of detecting an object (antigen) in a sample through contact with the sample.

With regard to colloidal gold, it is considered that the colloidal gold of the present invention includes colloidal platinum as well as colloidal gold.

The particle diameter of colloidal gold particles is known to significantly affect the measurement sensitivity, and for example, when the colloidal gold particles are retained and used in an immunochromatographic test strip, the particle diameter of colloidal gold particles is preferably 20 nm to 60 nm, more preferably 30 nm to 50 nm, and particularly preferably 40 nm. The colloidal gold may be manufactured by a generally known method, for example, by dropping and stirring a trisodium citrate aqueous solution or a triammonium citrate aqueous solution in a heated tetrachloroauric (III) acid aqueous solution. In this description, colloidal gold is also referred to as a colloidal gold particle(s), which has the same meaning.

(Sensitization of Colloidal Gold With Antibody)

Immobilization of an anti-analyte antibody to colloidal gold is generally achieved by physical adsorption. In this regard, the concentration of the antibody is preferably prepared at a concentration of 1 to 5 µg/mL buffer solution. The type and pH of the buffer solution are preferably 2 mmol/L phosphate buffer solution (pH 6.5 to pH 8) or 2 to 10 mmol/L Tris-hydrochloric acid buffer solution (pH 7 to pH 9), and more preferably 2 to 10 mmol/L Tris-hydrochloric acid buffer solution (pH 7 to pH 7.5); however, another buffer solution may be used without any limitation thereto. In this description, the above-described colloidal gold, onto which an antibody against an analyte or a control antibody (or antigen) is immobilized, is called a "conjugate".

(Blocking)

The conjugate of the present invention may be blocked by a blocking agent in the region of a colloidal gold surface not bound with an antibody.

The blocking agent of the colloidal gold conjugate is generally a component derived from an organism, and the component derived from an organism may be any component as long as it is derived from an organism and has a blocking effect, and for example, the component includes an animal protein or a peptide derived from an animal protein. Specifically, the component derived from an organism may be bovine serum albumin (BSA), Blocking Peptide Fragment (manufactured by TOYOBO) derived from microorganisms, NEO PROTEIN SAVER (manufactured by TOYOBO) derived from silk protein (hydrolysate of sericin), Starting Block™ (PBS) Blocking Buffer (manufactured by PIERCE), StabilCoat™ (manufactured by SurModics), and casein.

The concentration of a component derived from an organism may be appropriately determined depending on the component to be used. For example, an antibody solution is added to and mixed with a colloidal gold solution adjusted to 1 OD/mL, and then the component derived from an organism is added to the mixed solution to a final concentration within a range of 0.1% to 10% for blocking, and more preferably used within a range of 0.2% to 5%.

Alternatively, a mixture of both a component not derived from an organism and a component derived from an organism may be used as a blocking agent of colloidal gold.

(Detection Reagent)

In the present invention, a "detection reagent" is specifically a solution containing at least a conjugate.

The detection reagent may contain, for example, one or more stabilizers, solubilizing agents, etc., for the purpose of maintaining the conjugate in a stable state so as to facilitate the specific reaction between the antibody immobilized to the conjugate and the analyte or to make the conjugate dissolved and fluidized promptly and effectively when mixed with the sample. The stabilizers, solubilizing agents, etc. may include, for example, bovine serum albumin (BSA), sucrose, casein, amino acids, etc.

The detection reagent may also contain a known sensitizer such as 2-methacryloyloxyethyl phosphorylcholine for the purpose of improvement in detection sensitivity, as needed.

The detection reagent may also contain EDTA or EGTA that is a chelating agent of $Ca^{2+}$ ions, as needed.

The term "detection" or "measurement" as used herein must be construed in the broadest sense including verification and/or quantification of the presence of the analyte and must not be construed in a limited manner in any sense.

(Diluting Solution)

A diluting solution may be used in the present invention if dilution of a sample is required depending on the concentration of an analyte in the sample. The diluting solution may be a diluting solution of any composition as long as the diluting solution does not significantly inhibit the antigen-antibody reaction, or conversely, does not significantly facilitate the reaction resulting in excessive agglutination causing a defect of spread by capillarity, and does not make it impossible to detect signals of the antigen-antibody reaction in an antigen-concentration dependent manner.

The diluting solution having such an effect may be, for example, purified water, physiological saline, and a low-concentration buffer solution at pH 6.0 to pH 10.0, for example, 10 mmol to 20 mmol/L phosphate buffer solution, 10 mmol to 20 mmol/L Tris-HCl buffer solution, and 10 mmol to 20 mmol/L Bis-Tris buffer solution. A surfactant may be added to these diluting solutions so as to control the spread rate of the sample in the strip.

The diluting solution of the present invention may contain polybrene as a hemagglutinating agent as described above.

The diluting solution of the present invention may also contain an additive having an ability to suppress agglutination of colloidal gold conjugates due to polybrene, as described above.

(Sample Pad)

In the present invention, a "sample pad" is a part that serves as a sample supply portion receiving a sample, and is shaped into a pad to absorb a liquid sample, and the sample pad may be made of any material and in any form allowing the passage of liquid and the component to be detected.

The sample pad of the present invention may contain the hemagglutinating agent as described above. In this case, the hemagglutinating agent may be contained at least in a part or entirety of the sample pad.

The sample pad of the present invention may also contain the particular additive as described above. In this case, the particular additive may be contained at least in a part of or entirety of the sample pad. If the sample pad of the present invention contains both a hemagglutinating agent and a particular additive, the sample pad may contain both at the same part or may contain at respective different parts to avoid coexistence. The sample pad may entirely contain both of them.

Specific examples of materials suitable for the sample pad include, but are not limited to, a glass fiber, an acrylic fiber, a hydrophilic polyethylene material, a dry paper, a paper pulp, a fabric, etc. A glass fiber pad is preferably used. The sample pad may additionally be given the function of a conjugate pad described later. The sample pad may contain a commonly used blocking reagent as needed within a range not affecting the reaction system and not departing from the object of the present invention.

(Conjugate Pad)

The "conjugate pad", as used herein, refers to a pad which is obtained by impregnating a material suitable for the conjugate pad described later with a detection reagent specifically reactive with the analyte, followed by drying. The conjugate pad has a function of allowing the detection reagent and the analyte to form a complex when the sample passes through the conjugate pad. The conjugate pad may by itself be disposed in contact with an antibody-immobilized membrane. Alternatively, the conjugate pad may be disposed in contact with the sample pad so as to receive the sample which has passed through the sample pad by a capillary flow and then transfer the sample by a capillary flow to another pad (hereinafter also referred to as a "3rd pad") in contact with the surface different from the contact surface with the sample pad. The selection of one or more parts of the sample pad and the conjugate pad and how the selected parts are disposed on the antibody-immobilized membrane may be appropriately changed.

The conjugate pad of the present invention may also contain the particular additive as described above. In this case, the particular additive is contained at least in a part of the upstream side from a part to which the conjugate is immobilized, and may be contained in entirety of the conjugated pad.

Materials suitable for the conjugate pad may include, but are not limited to, paper, a cellulose compound, nitrocellulose, polyester, an acrylonitrile copolymer, a glass fiber, and a nonwoven fiber such as rayon. A glass fiber pad is preferably used.

The conjugate pad may contain, as needed, a "control reagent" for securing reliability of immunochromatography, for example, an antibody labeled with a label and not reactive with the sample component, or a highly antigenic protein such as KLH (keyhole limpet hemocyanin) labeled with a label. These control reagents are components (substances) having no possibility of being present in the sample and may appropriately be selected.

(3rd Pad)

In the present invention, a 3rd pad may be disposed for the purpose of removing components unnecessary for detection of the analyte among the components in the sample reacted with the detection reagent so that components necessary for reaction may smoothly spread in an insoluble membrane to which an antibody is immobilized.

For example, blood cells, insoluble blood cell fractures, etc. are preferably removed as the components unnecessary for detection. The 3rd pad may also be given an additional effect of preliminarily removing aggregates which are grown to such a size as to prevent the movement to and the smooth spread in the antibody-immobilized membrane out of aggregates generated by antigen-antibody reactions. The 3rd pad may be made of any material and in any form allowing the passage of liquid and the component to be detected.

Specific examples include, but are not limited to, a glass fiber, an acrylic fiber, a hydrophilic polyethylene material, a dry paper, a paper pulp, a fabric, etc.

In the present invention, a blood cell-separation membrane is preferably used for completely separating and removing blood cells which could not be removed only by the hemagglutinating agent and the sample pad described above.

(Immobilization of Antibody to Insoluble Membrane)

In an immunochromatographic reagent of the present invention, immobilization of an antibody against an analyte to an insoluble membrane may be performed by a generally well-known method. For example, in the case of the flow-through format, an antibody is prepared at a predetermined concentration and a given amount of the solution thereof is applied to the insoluble membrane in a shape of a specific symbol such as dot or "+". In this case, to secure reliability of immunochromatography, a "control line" is generally formed by immobilizing a protein or a compound capable of binding to the conjugate to a position different from the antibody against the analyte. The "control line" may be formed by immobilizing the antibody against the control reagent to a position different from the antibody against the analyte.

In the case of a lateral-flow format, an antibody is prepared at a predetermined concentration and the solution thereof is applied to an insoluble membrane in a line shape by using a device capable of horizontally moving while discharging the solution from a nozzle at a constant rate. In this regard, the concentration of the antibody is preferably 0.1 mg/mL to 5 mg/mL, and more preferably 0.5 mg/mL to 3 mg/mL. The immobilized amount of the antibody on the insoluble membrane may be optimized by adjusting the application amount dropped onto the insoluble membrane in the case of the flow-through format, and optimized by adjusting the discharge rate from the nozzle of the device in the case of the lateral-flow format. Particularly, in the case of the lateral-flow format, 0.5 µL/cm to 2 µL/cm is preferable. In the present invention, a "flow-through membrane assay" refers to a format in which the sample liquid, etc. spreads to perpendicularly pass through the insoluble membrane, and a "lateral-flow membrane assay" refers to a format in which the sample liquid, etc. spreads to move laterally along the insoluble membrane.

In the present invention, the application position of an antibody against an analyte to the insoluble membrane may be placed such that the detection reagent spreads from the conjugate pad by capillarity and sequentially passes through the lines to which the respective antibodies are applied in the case of the lateral-flow format. Preferably, the line formed by applying the antibody against the analyte is preferably located upstream while the line formed by applying a control antibody is located downstream thereof. In this case, a sufficient distance is preferably placed between the respective lines such that signals of labels may be detected. In the case of the flow-through format, the position of application of the antibody against the analyte may be placed such that signals of labels may be detected.

The antibody solution applied to the insoluble membrane may normally be prepared by using a predetermined buffer solution. The type of the buffer solution may include commonly used buffer solutions such as a phosphate buffer solution, a Tris buffer solution, a Good's buffer solution, etc. pH of the buffer solution is preferably in a range of 6.0 to 9.5 and may be appropriately determined depending on properties of the antibody to be used. For example, a buffer solution of pH 7.2 is usable for an anti-H-FABP monoclonal antibody described later. The buffer solution may contain a salt such as NaCl, etc., a stabilizer and a preservative such as sucrose, and antiseptic such as ProClin, etc. The salt may include those contained for adjusting ionic strength, such as NaCl, as well as those added at the step of adjusting pH of the buffer solution, such as sodium hydroxide. After the antibody is immobilized to the insoluble membrane, blocking may be performed by coating a portion other than the antibody-immobilized parts with a commonly used blocking agent in a solution or in a vapor state.

In this description, the insoluble membrane having the antibody immobilized as described above is also referred to as an "antibody-immobilized membrane".

(Insoluble Membrane)

In the present invention, the insoluble membrane (hereinafter, also simply referred to as a membrane) may be made of any material. For example, the materials may include, but are not limited to, polyethylene, polyethylene terephthalate, nylons, glass, polysaccharide such as cellulose and cellulose derivatives, or ceramics. Specifically, the materials may include glass fiber filter papers and cellulose filter papers available from Merck & Co., Inc., Toyo Roshi, kaisha, Ltd., Whatman, Inc., etc. The pore size and structure of the insoluble membrane may be appropriately selected, thereby controlling the flow speed of an immune complex of a colloidal gold-labeled antibody and an object through the membrane. The amount of the labeled antibody binding to the antibody immobilized to the membrane can be adjusted by controlling the flow speed through the membrane, and therefore, the pore size and the structure of the membrane are preferably optimized in consideration of combinations with the other constituent materials of the immunochromatographic test strip of the present invention.

(Absorption Pad)

In the present invention, the absorption pad refers to a liquid-absorbing part that absorbs the sample which has moved on and passed through the insoluble membrane to control the spread of the sample. The absorption pad may be disposed at the most downstream portion of the strip configuration in the lateral-flow format, and may be disposed on, for example, the lower portion of the antibody-immobilized membrane in the flow-through format. The absorption pad may be made of, for example, filter paper, but is not limited thereto. Preferably, 740-E of Whatman, Inc., etc. is used.

(Detection Device)

The immunochromatographic test strip of the present invention may be used after being installed/mounted in an appropriate container (housing) in consideration of the size of the strip, the addition method and position of the sample, the immobilization position of antibody on the antibody-immobilized membrane, the signal detection method, etc., and such an installed/mounted state is referred to as a "device".

(Others)

In this description, the "insoluble membrane" is also referred to as a "solid phase", and allowing or a state of allowing the insoluble membrane to physically or chemically support antigens or antibodies may be expressed as "immobilization", "immobilized", "solid-phased", "sensitization", or "adsorption".

(Sample)

In the detection method of the present invention, a "sample" containing an analyte is a liquid containing a particulate component having a large number of negative charges on the surface, and biological samples may include liquids containing red blood cells, particularly, whole blood, red blood cells separated by centrifugation, blood plasma, etc.

Further, the blood sample includes a sample collected by a collection tube containing an anticoagulant such as EDTA, heparin, etc. at the time of collecting blood (hereinafter, simply referred to as an EDTA-containing sample, a heparin-containing sample, etc.).

According to the present invention, a problem that a measured value of an EDTA-containing sample is lower than that of a heparin-containing sample in immunochromatography is solved, and an effect that accurate measurement may be made regardless of the kind of the sample is also obtained. Further, an effect of increasing detection sensitivity may be obtained by the additive of the present invention. Therefore, it is also possible to control the detection sensitivity of the immunochromatographic device by selecting the concentration or type of the additive as desired.

(Analyte)

The analyte of the present invention is a substance present in a biological sample such as blood (whole blood), red blood cells, serum, plasma, urine, saliva, sputum, etc., and is exemplified by inflammation related markers such as CRP (C-reactive protein), IgA, IgG, IgM, etc., coagulation/fibrinolysis markers such as fibrin degradation products (e.g., D-dimer), soluble fibrin, TAT (thrombin-antithrombin complex), PIC (a plasmin-plasmin inhibitor complex), etc., circulation related markers such as oxidized LDL, BNP (brain natriuretic peptide), H-FABP (heart-type fatty acid-binding protein), etc., metabolism related markers such as adiponectin, etc., tumor markers such as CEA (carcinoembryonic antigen), AFP ($\alpha$-fetoprotein), CA19-9, CA125, PSA (prostate-specific antigen), etc., infection related markers such as HBV (hepatitis B virus), HCV (hepatitis C virus), Chlamydia trachomatis, gonococcus, etc., allergen-specific IgE (immunoglobulin E), hormones, drugs, etc. Among them, D-dimer, CRP, BNP, H-FABP, etc., which are highly desired to use whole blood as a sample, are more preferred.

(Antibody Used in the Present Invention)

The antibody against the analyte used in the present invention is not limited in any way to a preparation method as long as the antibody is specifically reactive to the analyte, and may be a polyclonal antibody or a monoclonal antibody. A hybridoma producing an antibody may be generally prepared by cell fusion between spleen cells of an animal immunized with an analyte as an immunogen and myeloma cells from the same species in accordance with the method of Kohler and Milstein (see Nature, Vol. 256, p. 495, 1975).

When antibodies used in a measurement method of detecting an analyte through formation of so-called sandwich are monoclonal antibodies, a relationship between a label-immobilized antibody (first antibody) and an insoluble membrane-immobilized antibody (second antibody) is such that the epitope of the second antibody is different from the first antibody if the epitope of the first antibody is monovalent, and the epitope of the second antibody may be the same as or different from the first antibody if the epitope of the first antibody is multivalent.

In Example 1 described later, an anti-H-FABP monoclonal antibody was used. Although a method of preparing the anti-H-FABP monoclonal antibody used in the present invention is as described in the next section, the present invention is not limited thereto, and a commercially available H-FABP monoclonal antibody may also be used. Examples of the commercially available H-FABP monoclonal antibodies may include clones #5B5, #10E1, etc. of HyTest, and clones #M79188, #M79189, etc. of Fitzgerald (It is noted that monoclonal antibodies may be denoted by clone names of hybridomas producing the respective antibodies for convenience. The same applies hereinafter).

(Preparation Example of Anti-H-FABP Monoclonal Antibody)

(1) Preparation of Hybridoma

Human purified H-FABP (manufactured by HyTest) dissolved in PBS was used as an immunogen. This immunogen was mixed and emulsified with complete Freund's adjuvant (manufactured by Wako Pure Chemical Industries) at a ratio of 1 to 1 in a fluid volume to prepare an emulsion having the H-FABP concentration of 0.5 mg/mL, and 100 µL of the emulsion was subcutaneously administered to a 6-week-old female BALB/C mouse. Subsequently, 100 µL of emulsion having 0.2 mg/mL of the H-FABP concentration was additionally administered three times for two and a half months, and after 10 days from the third additional administration, 100 µL of 0.2 mg/mL human purified H-FABP dissolved in PBS was subcutaneously administered. Three days later, the spleen, the groin lymph nodes, and the iliac lymph nodes were excised, and the obtained spleen and lymph node cells were mixed with myeloma cells SP2/O—Ag14 at a ratio of 6 to 1 for cell fusion in the presence of 50% polyethylene glycol 1540 (manufactured by Wako Pure Chemical Industries). The fused cells were suspended in HAT medium at a density of spleen cells of $2.5 \times 10^6$/mL and dispensed by 0.2 mL to a 96-well culture plate (manufactured by CORNING). These cells were cultured in a 5% $CO_2$ incubator at 37° C., and after about 1 week, strains which produce antibodies reactive to H-FABP were selected by using the culture supernatant of wells with growing hybridomas in an ELISA method. Specifically, first, IgG in each of the culture supernatants was solid-phased via goat anti-mouse IgG (Fc) antibodies (manufactured by JACKSON) on a microplate (manufactured by NUNC) and then reacted with H-FABP. Subsequently, reaction was performed with biotin-labeled anti-H-FABP rabbit polyclonal antibodies (manufactured by Proteintech Group) and also with peroxidase-labeled streptavidin (manufactured by PIERCE). Thereafter, a peroxidase substrate solution containing ortho-phenylenediamine (manufactured by Tokyo Chemical Industry) was added for color development, and the color development was stopped by adding 1.5 N sulfuric acid, and then measurement was performed by a microplate reader (Abs. 492 nm) to select hybridomas exhibiting high reactivity to H-FABP. Selected hybridomas were cloned with a limiting-dilution method to establish 10 types of anti-H-FABP monoclonal antibody-producing hybridomas.

(2) Preparation of Monoclonal Antibody

The hybridomas obtained in (1) were intraperitoneally administered in an amount of $0.2 \times 10^5$ cells to a 12-week-old female BALB/C mouse which had been intraperitoneally injected with 0.5 mL of pristane two weeks before. After about 14 days, the ascites was collected, and supernatant was obtained by centrifugation. The supernatant was mixed with the same amount of an adsorption buffer solution (3 mol/L NaCl-1.5 mol/L Glycine-NaOH, pH 8.5) and then filtrated. The filtrate was passed through a protein A column (manufactured by GE Healthcare) equilibrated with the adsorption buffer solution to adsorb antibodies in the filtrate onto the column, and then the antibodies were eluted with 0.1 mol/L citrate buffer solution (pH 3.0) from the column and the anti-H-FABP monoclonal antibodies (Clone #87203 and Clone #87212) were purified.

(Measurement)

A method of quantifying signals derived from colloidal gold may be performed in accordance with a known method, and absorbance or reflected light intensity may be measured. Alternatively, the changes in absorbance or reflected light intensity may be extrapolated to a calibration curve of samples with known concentrations to measure the concentration of the object.

(Detection Method Using Immunochromatography)

The detection method using immunochromatography of the present invention is a method including at least the following steps of (A) to (E), and is typically a detection method using the immunochromatographic test strip described above:

(A) a step of supplying a sample to a sample supply portion of a test strip comprising a membrane consisting of a porous body equipped with at least the sample supply portion, a spreading portion, and a detecting portion, wherein a colloidal gold-labeled antibody against an analyte (conjugate) is retained in a dissoluble manner in a part of the spreading portion, and an immobilized antibody is immobilized in the detecting portion which is a part of the spreading portion on the downstream side relative to the conjugate-retaining part;

(B) a step of agglutinating a blood-derived component in the sample through contact between polybrene and the sample in the sample supply portion or in the upstream of the sample supply portion;

(C) a step of separating and removing aggregates obtained in step (B) from the sample;

(D) a step of bringing a sample component obtained in step (C), from which the aggregates are separated and removed, into contact with the colloidal gold-containing conjugate, this step being performed in the presence of an additive having an ability to suppress agglutination of the conjugate due to polybrene; and (E) a step of detecting a complex of the analyte in the sample component and the conjugate obtained in step (D) in the detecting portion.

EXAMPLES

The present invention will be described in detail with reference to the following Examples. However, the scope of the present invention is not limited thereto.

[Example 1] Selection Method of Additive of the Present Invention

An absorption wavelength of a mixed solution of a polybrene solution and a conjugate solution containing an additive candidate of the present invention was measured to select the additives of the present invention.

1. Preparation of Various Solutions and Conjugate

1) Preparation of Colloidal Gold-Labeled Anti-H-FABP Monoclonal Antibody (Anti-H-FABP Antibody Conjugate)

(i) Preparation of Colloidal Gold Solution

To 500 mL of purified water heated to 73° C., 1 mL of a 5% (w/v) triammonium citrate aqueous solution was added and then mixed under stirring. Subsequently, 1 mL of a 5% (w/v) tetrachloroauric(III) aqueous solution was added and reacted for 10 minutes under stirring and the reaction solution was then boiled. Thereafter, the reaction solution was cooled in ice water and a solution of colloidal gold with an average particle diameter of 40 nm was prepared. This solution of colloidal gold having an average particle diameter of 40 nm was adjusted to 1 OD/mL of absorbance at the local maximum absorption wavelength of colloidal gold by using a 2 mmol/L Tris-HCl buffer solution (pH 7.0).

(ii) Preparation of Anti-H-FABP Antibody Conjugate

To 20 mL of the 1 OD/mL colloidal gold solution (pH 7.0), 1 mL of the anti-H-FABP monoclonal antibody (F(ab')$_2$ fragment of Clone #87212) diluted to 46.2 µL/mL with a 2 mmol/L Tris-HCl buffer solution (pH 7.0) was added and stirred at room temperature for 10 minutes. To the mixed solution of the colloidal gold and the antibody, 1 mL of a 2 mmol/L Tris-HCl buffer solution (pH 7.0) containing a 0.1% (w/v) blocking agent (NEO PROTEIN SAVER: TOYOBO Biochemical, No. NPS-301) was added and stirred at room temperature for 5 minutes. The mixed solution was then centrifuged at 10° C. at 11900×g for 45 minutes.

After supernatant was removed, 1 mL of a conjugate dilution buffer (SCRIPPS, No. B0221) was added to the obtained precipitate to suspend the conjugate, thereby obtaining an anti-H-FABP antibody conjugate.

(iii) Preparation of Additive Solution

Each of the additives described in Table 1 was dissolved in water. Each of the additives was adjusted to 1 mol/L or 0.5 mol/L according to its solubility for water.

(iv) Preparation of Test Suspension

The above-prepared additive solution was added to the anti-H-FABP antibody conjugate prepared in (ii), and the additives were adjusted to be at various concentrations, and this suspension was used as a test suspension. The combination of the concentration of the additive in each test suspension is shown in Table 1.

(v) Polybrene Aqueous Solution

Polybrene (Sigma-Aldrich) was dissolved in water and prepared as a 0.5% aqueous solution.

TABLE 1

| | Category | | Additive candidate | Concentration (mM) | |
|---|---|---|---|---|---|
| (A) Salt of divalent metal | (A1) Salt of divalent metal with acid | | Magnesium sulfate | 2 | Example 1 (A1-1a) |
| | | | | 10 | Example 1 (A1-1b) |
| | | | | 15 | Example 1 (A1-1c) |
| | | | Magnesium nitrate | 10 | Example 1 (A1-2) |
| | | | Magnesium acetate | 10 | Example 1 (A1-3) |
| | (A2) Salt of divalent metal with halogen element | | Magnesium chloride | 10 | Example 1 (A2-1) |
| | | | Calcium chloride | 15 | Example 1 (A2-2) |
| | | | Zinc chloride (II) | 15 | Example 1 (A2-3) |
| | | | Manganese chloride (II) | 15 | Example 1 (A2-4) |
| | | | Nickel chloride (II) | 15 | Example 1 (A2-5) |

TABLE 1-continued

| Category | | Additive candidate | Concentration (mM) | |
|---|---|---|---|---|
| (B) Salt of sulfuric acid with metal or onium | (B1) Salt of sulfuric acid with metal | Potassium sulfate | 10 | Example 1 (B1-1) |
| | | Magnesium sulfate | 2 to 15 | Example 1 (B1-2a to c) *overlapped with Example 1 (A1-1a to c) |
| | (B2) Salt of sulfuric acid with onium | Ammonium sulfate | 10 | Example 1 (B2) |
| (C) Salt of sulfurous acid with metal | | Sodium sulfite | 10 | Example 1 (C) |
| (D) Carboxylic acid chelator | (D1) Carboxylic acid | DTPA | 15 | Example 1 (D1-1) |
| | | Oxalic acid | 15 | Example 1 (D1-2) |
| | | Tartaric acid | 15 | Example 1 (D1-3) |
| | | Succinic acid | 15 | Example 1 (D1-4) |
| | (D2) Salt with metal | EDTA•2Na | 10 | Example 1 (D2-1) |
| | | Citric acid•3Na | 10 | Example 1 (D2-2) |
| (E) Polybasic amino acid | | Poly-L-arginine hydrochloride | (10%) | Example 1 (E) |
| Carbonate or bicarbonate | | Sodium carbonate | 10 | Comparative Example 1-1 |
| | | Ammonium bicarbonate | 15 | Comparative Example 1-2 |
| Salt of monovalent metal with halogen element | | Lithium chloride | 15 | Comparative Example 2-1 |
| | | Sodium chloride | 10 | Comparative Example 2-2 |
| | | Potassium chloride | 15 | Comparative Example 2-3 |
| Amino acid | Amino acid | Glutamic acid | 10 | Comparative Example 3-1 |
| | | Aspartic acid | 10 | Comparative Example 3-2 |
| | Amino acid metal salt | Sodium glutamate | 15 | Comparative Example 3-3 |
| | | Sodium Aspartate | 15 | Comparative Example 3-4 |
| Other | | Choline chloride | 10 | Comparative Example 4 |

2. Test Method

The absorption wavelength was measured at the time of adding the polybrene aqueous solution to the test suspension.

An equal volume of a 0.5% polybrene aqueous solution was added to the test suspension prepared above, and then 1.5 minutes immediately after the addition of the polybrene aqueous solution, absorbance was measured with a spectrophotometer in the range of 400 nm to 900 nm, and a local maximum absorption wavelength was calculated from the spectrum of the measured absorption wavelengths. If the obtained local maximum absorption wavelength is smaller than the local maximum absorption wavelength in the case of no addition of additives (that is, agglutination of colloidal gold conjugates), it may be determined that each additive has the effect of reducing agglutination in the presence of polybrene. Further, if the obtained local maximum absorption wavelength is close to a local maximum absorption wavelength in the case of no polybrene (that is, no agglutination of colloidal gold conjugates), it may be determined that the additive is preferred.

3. Test Results

Each local maximum absorption wavelength is shown in FIG. 1. The concentration of the additive described in FIG. 1 is the concentration of the test suspension in Table 1. Hereinafter, each sample is identified with and evaluated at this concentration.

The local maximum absorption wavelength of the sample was 552 nm without additives in the presence of polybrene. On the contrary, all samples to which the additive of Example was added in the presence of polybrene showed the local maximum absorption wavelengths shorter than that of the sample without the additive, and the wavelengths were near the local maximum absorption wavelength of the sample in the absence of polybrene.

On the other hand, some of the compounds of Comparative Examples showed the local maximum absorption wavelengths shorter than the local maximum absorption wavelength of the sample without the additive in the presence of polybrene, but the degree was slight and some of them showed the local maximum absorption wavelengths longer than the local maximum absorption wavelength of the sample without the additive in the presence of polybrene.

[Example 2] Comparison Between Immunochromatographic Method Using the Additive of the Present Invention and LTIA Method 1. Production of Immunochromatographic Device of the Present Invention 1) Preparation of Colloidal Gold-Labeled Anti-H-FABP Monoclonal Antibody (Anti-H-FABP Antibody Conjugate)

(i) Preparation of Colloidal Gold Solution

A colloidal gold solution prepared in the same manner as in (i) of Example 1 was used.

(ii) Preparation of Anti-H-FABP Antibody Conjugate

An anti-H-FABP antibody conjugate prepared in the same manner as in (ii) of Example 1 was used.

(iii) Preparation of Colloidal Gold-Labeled KLH (KLH Conjugate) for Control Line To 20 mL of the 1 OD/mL colloidal gold solution (pH 6.1), 1 mL of KLH (manufactured by Sigma) dissolved to 620 μg/mL with a 2 mmol/L phosphate buffer solution (pH 6.1) was added and stirred at room temperature for 10 minutes. To the mixed solution of the colloidal gold and KLH, 1 ml of a 10% bovine serum albumin (BSA) solution was added and stirred at room temperature for 5 minutes. The mixed solution was then centrifuged at 10° C. at 11900×g for 45 minutes. After the supernatant was removed, 1 mL of the conjugate dilution buffer mentioned above was added to the obtained precipitate to suspend the conjugate, thereby obtaining KLH conjugate.

2) Production of Conjugate Pad

To the anti-H-FABP antibody conjugate prepared in 1), magnesium sulfate (30 mmol/L, 50 mmol/L), magnesium acetate (30 mmol/L, 50 mmol/L), or ammonium sulfate (30 mmol/L) was added as additives, respectively. The concentration of each additive was a final concentration.

The anti-H-FABP antibody conjugate containing each of the additive was adjusted to 3 OD/mL and the KLH conjugate was adjusted to 0.75 OD/mL by mixing with a Tris-HCl buffer solution containing 2.5% NEO PROTEIN SAVER and 2.4% lactose, thereby preparing conjugate solutions. A certain volume of a glass fiber pad (Pall Corporation, Japan, No. 8964) was impregnated with 1.2 volumes of the conjugate solutions relative to the volume of the pad. The pad was heated and dried at 70° C. for 45 minutes in a dry oven to obtain a conjugate pad. If an additive such as a sensitizer is added as needed, a necessary amount may be added to the conjugate solutions before performing the same operation.

Separately from the test above (test (A)), a conjugate pad was produced in the same manner as above, except that the concentration of magnesium sulfate as the additive was changed to 10 mmol/L. Further, a conjugate pad without additives (conventional formulation) was produced (test (B)).

3) Production of Anti-H-FABP Monoclonal Antibody-Immobilized Membrane (Antibody-Immobilized Membrane)

The anti-H-FABP monoclonal antibody (Clone #87203) was prepared to a concentration of 3 mg/mL by dilution with a 10 mmol/L phosphate buffer solution (pH 7.2) containing 2.5% sucrose, and a rabbit anti-KLH polyclonal antibody (manufactured by Bethyl) was prepared to a concentration of 0.5 mg/mL by dilution with a 10 mmol/L phosphate buffer solution (pH 7.2) containing 2.5% sucrose for the purpose of color development of the control line. The anti-H-FABP monoclonal antibody was applied onto a nitrocellulose membrane (Merck, HF180, 260 mm×25 mm) at a position inside one end of a short side and the anti-KLH polyclonal antibody was applied at an interval of about 5 mm from the position above by using an immunochromatography dispenser "XYZ3050" (BIO DOT) set to 1 µL/cm in a line shape. The membrane was dried at 70° C. for 45 minutes in a dry oven to obtain an antibody-immobilized membrane.

4) Production of Sample Pad

A glass fiber pad (Lydall) was appropriately cut to a necessary size, and impregnated with the same buffer solution (or purified water) as for the conjugate pad containing 1% polybrene at 1.15 volumes relative to a volume of the pad, and was dried at 70° C. for 45 minutes in a dry oven, and the pad was used as a sample pad.

5) Production of Immunochromatographic Test Strip

To a plastic adhesive sheet (a), the antibody-immobilized membrane (b) was attached such that antibody-application sites were arranged in the order of the anti-H-FABP antibody (c) on the upstream side of spread and then the anti-KLH antibody (d), and a blood cell-separating membrane (3rd pad) (e) was further mounted. The conjugate pad (f) produced in 2) was then disposed and mounted, and the sample pad (g) produced in 4) was disposed and mounted to overlap the conjugate pad while the absorption pad (h) was disposed and mounted on the end of the other side. An immunochromatographic test strip was produced by cutting into a structure having the constituting elements overlapped with each other as described above. The test strip was installed/mounted in a dedicated plastic housing (having a sample-addition window and a detection window not shown in FIG. 2) at the time of an assay to implement a form of an immunochromatographic test device. FIG. 2 is a schematic structure of the immunochromatographic test strip.

6) Measurement by Immunochromatographic Method

To the sample pad window of the above immunochromatographic test device, 120 µL of the sample was added, and 10 minutes later, the reflected light intensity of anti-H-FABP antibody-application site (detecting portion) in the test device was measured by using an immunochromato-reader RAPID PIA (Hamamatsu Photonics). The concentration of H-FABP was calculated from the reflected light intensity.

2. Measurement by LTIA Method

Measurement by the LTIA method was carried out with an automatic analyzer, Hitachi 7170 (Hitachi, Ltd.) using an LTIA measurement reagent, LIBLIA (registered trademark) H-FABP (DS Pharma Biomedical Lot. S1 KH 06). The operation was carried out according to the attached document of LIBLIA H-FABP and the instruction manual of Hitachi 7170. The H-FABP concentration of each sample quantified by the automatic analyzer was obtained.

3. Sample

Plasma samples (simply referred to as heparin-containing samples in this Example and in the following Example) collected by using blood collection tubes to which heparin was added at the time of blood collection were 24 samples for test (A) and 17 samples for test (B). Plasma samples (simply referred to as EDTA-containing samples in this Example and in the following Example) collected by using blood collection tubes to which EDTA was added at the time of blood collection were 22 samples for test (A) and 29 samples for test (B).

4. Test Results

With respect to each sample, the H-FABP concentration obtained by immunochromatography was plotted on the Y axis and the H-FABP concentration obtained by the LTIA method on the X axis, and the influence of each additive on the correlation of the two measurement methods was shown. The results are shown in FIG. 3.

In the conventional method, that is, when no additive was added, the EDTA-containing sample had a lower value than the heparin-containing sample. In contrast, when any of the additives was added, the correlations of the EDTA-containing sample and the heparin-containing sample were closer than those of the conventional method.

In immunochromatography, when the conventional formulation, that is, no additive was used, the EDTA-containing sample had a lower value than the heparin-containing sample. On the contrary, when a formulation of adding the additive of the present invention was used, the problem of the lower value of the EDTA-containing sample was solved in any case, and the correlations of both the EDTA-containing sample and the heparin-containing sample with the LTIA method were similar.

[Example 3] Comparison of Detection Sensitivity Between Additive Formulation of the Present Invention and Conventional Formulation 1. Production of Immunochromatographic Device For the additives in 1. 2) Production of Conjugate Pad (A) of Example 2, conjugate pads containing the respective additives such as magnesium sulfate at a concentration of 30 mmol/L or 50 mmol/L, magnesium acetate at a concentration of 30 mmol/L or 50 mmol/L, and ammonium sulfate at a concentration of 30 mmol/L were produced, and a conjugate pad without additives (conventional formulation) was produced in the same manner (A).

In the same manner as above, conjugate pads containing the respective additives were produced, except that magnesium sulfate was used at a concentration of 10 mmol/L or 50 mmol/L, and magnesium chloride was used at a concentration of 50 mmol/L, and a conjugate pad without additives (conventional formulation) was produced (B).

In both cases (A) and (B) above, an immunochromatographic device was produced in the same manner as in Example 2, except for the method of producing the conjugate pad. In the case of (B), however, a device including neither the additive nor polybrene was also produced.

2. Sample

Heparin-containing samples were 24 samples for test (A) and 17 samples for test (B) (however, magnesium sulfate of 50 mmol/L and magnesium chloride of 50 mmol/L were only 10 samples), and EDTA-containing samples were 22 samples for test (A) and 29 samples for test (B).

3. Test Method

In the same manner as in Example 2, 120 µL of the sample was added to the sample pad window of the above immunochromatographic test device, and 10 minutes later, the reflected light intensity of anti-H-FABP antibody-application site (detecting portion) in the test device was measured by using an immunochromato-reader RAPID PIA (Hamamatsu Photonics). The reflected light intensity for each sample in the device without the additives was taken as 100%, and a ratio of the reflected light intensity of the device, to which each additive was added, was calculated, and an average value of the ratio was obtained.

4. Test Results

The results are shown in FIG. 4

When EDTA-containing samples were measured in the device to which any additives were added, the reflected light intensity was increased, as compared with the device without the additives ((A): 122.1% to 128.5%, (B): 118.6% to 126.9%). In addition, even when heparin-containing samples were measured, certain increase of reflected light intensity was also confirmed in the devices, to which magnesium sulfate, magnesium acetate, and ammonium sulfate were added ((A): 102.6% to 110.4%, (B): 100.5% for magnesium sulfate of 10 mmol/L, 102.9% for magnesium sulfate of 50 mmol/L).

INDUSTRIAL APPLICABILITY

According to the present invention, in immunochromatography using polybrene as a hemagglutinating agent and a colloidal gold conjugate as a detection reagent, red blood cells may be agglutinated and then separated and removed from a sample without agglutination of colloidal gold by using a particular additive, and therefore, an object in the sample may be accurately detected and measured. Since addition of a polyanion as a neutralizer for polybrene is not needed, composition of reagents may be made extremely simple.

REFERENCE SIGNS LIST (a) Plastic adhesive sheet
(b) Antibody-immobilized membrane
(c) Anti-H-FABP antibody
(d) Anti-KLH antibody
(e) Blood cell-separating membrane (3rd pad)
(f) Conjugate pad
(g) Sample pad
(h) Absorption pad

The invention claimed is:

1. An immunochromatographic test strip, comprising:
   (1) a membrane comprising a porous body, which comprises a sample-supply portion and a spreading portion, wherein the sample-supply portion is upstream from the spreading portion,
   wherein hexadimethrine bromide is contained in the sample supply portion, and
   wherein a conjugate of an anti-analyte antibody labeled with colloidal gold is retained in a dissoluble manner in a conjugate-retaining part of the spreading portion, and an antibody is immobilized in a detecting part of the spreading portion, which is downstream from the conjugate-retaining part; and
   (2) an additive in a dry state, wherein the additive is contained in the sample-supply portion or the conjugate-retaining part of the spreading portion so as to be capable of contacting with hexadimethrine bromide that is provided through the sample-supply portion,
   wherein the additive is one or more compounds selected from the group consisting of (A) a salt of a divalent metal, (B) a salt of sulfuric acid with a metal or onium, (C) a salt of sulfurous acid with a metal, and (E) a polybasic amino acid,
   wherein a polyanion as a neutralizer for neutralizing a cation of the hexadimethrine bromide is not included on the test strip.

2. The test strip of claim 1, wherein the additive is contained in the conjugate-retaining part.

3. A detection method of using immunochromatography, comprising the steps of:
   (A) supplying a sample to a sample-supply portion of a test strip, said test strip comprising a membrane, said membrane comprising a porous body, which comprises the sample-supply portion and a spreading portion,
   wherein the sample-supply portion is upstream from the spreading portion,
   wherein hexadimethrine bromide is contained in the sample-supply portion,
   wherein a conjugate comprising an anti-analyte antibody immobilized on colloidal gold is retained in a dissoluble manner in a conjugate-retaining part of the spreading portion, and an antibody is immobilized in a detecting part of the spreading portion, which is downstream from the conjugate-retaining part,
   wherein a polyanion as a neutralizer for neutralizing a cation of the hexadimethrine bromide is not included on the test strip,
   wherein an additive is contained in the sample-supply portion or the conjugate-retaining part of the spreading portion in a dry state, and
   wherein the additive is one or more compounds selected from the group consisting of (A) a salt of a divalent metal, (B) a salt of sulfuric acid with a metal or onium, (C) a salt of sulfurous acid with a metal, and (E) a polybasic amino acid;
   (B) agglutinating red blood cells in the sample through contact between hexadimethrine bromide and the sample in the sample-supply portion;
   (C) separating and removing aggregates obtained in step (B) from the sample;
   (D) bringing a sample component obtained in step (C), after separation and removal of the aggregates, into contact with the colloidal gold-containing conjugate, step (D) being performed in the presence of the additive; and
   (E) detecting a complex of the analyte in the sample component and the conjugate obtained in step (D) with the antibody immobilized in the detecting portion.

4. The detection method of claim 3, wherein the additive is contained in the conjugate-retaining part.

5. The detection method of claim 3, wherein the sample is a heparin-containing sample or an EDTA-containing sample.

\* \* \* \* \*